United States Patent [19]

Leeper et al.

[11] 3,938,515

[45] Feb. 17, 1976

[54] NOVEL DRUG PERMEABLE WALL

[75] Inventors: Harold M. Leeper, Mountain View; Alan S. Michaels, Atherton, both of Calif.

[73] Assignee: Alza Corporation, Palo Alto, Calif.

[22] Filed: Oct. 19, 1973

[21] Appl. No.: 408,233

Related U.S. Application Data

[63] Continuation-in-part of Ser. No. 209,782, Dec. 20, 1971, abandoned.

[52] U.S. Cl. .............................. 128/260; 128/270
[51] Int. Cl.² A61F 5/46; A61F 13/20; A61M 31/00
[58] Field of Search ...... 128/130, 260, 270; 424/19, 424/22; 260/873

[56] References Cited
UNITED STATES PATENTS

| | | | |
|---|---|---|---|
| 3,039,933 | 6/1962 | Goldman et al. | 424/19 |
| 3,247,066 | 4/1966 | Milosovich, Jr. | 424/19 |
| 3,344,029 | 9/1967 | Berger | 424/19 |
| 3,538,214 | 11/1970 | Polli et al. | 424/19 |
| 3,580,965 | 5/1971 | Brinkmann et al. | 260/873 |
| 3,634,584 | 1/1972 | Poole | 424/19 |
| 3,675,648 | 7/1972 | Pharriss | 128/130 |
| 3,769,416 | 10/1973 | Smith et al. | 424/19 |

*Primary Examiner*—Aldrich F. Medbery
*Attorney, Agent, or Firm*—Thomas E. Ciotti; Paul L. Sabatine; Edward L. Mandell

[57] ABSTRACT

A polymeric wall adapted to release drug at a controlled rate for a prolonged period of time from a reservoir comprising a drug and a carrier which is permeable to the drug and saturated therewith during said prolonged period of time, to a body environment or a drug receptor site, the wall comprising a mixture of a polymer which is biologically compatible with said environment or site and maintains its integrity while in contact therewith, has a glass transition temperature between ambient temperature and 150°C, a crystallinity of 5% to 95%, or is rubbery, and is permeable to the drug but at a rate less than that of the carrier and as a minor constituent a polymeric additive such as a polyester prepared from a glycol and a dibasic acid, polyethylene glycol, chlorinated polyethylene or copolymers of ethylene and vinyl esters or vinyl esters or vinyl halides, the amount of additive being sufficient to make the permeability of the wall to the drug substantially different than the permeability of the polymer to the drug but still less than the permeability of the carrier to the drug.

7 Claims, 4 Drawing Figures

U.S. Patent  Feb 17, 1976  3,938,515
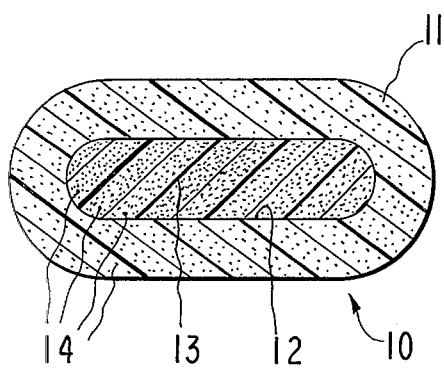
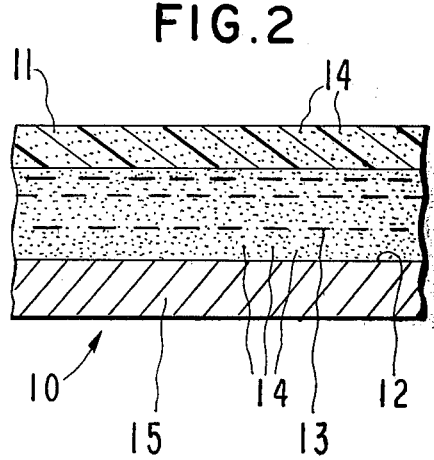
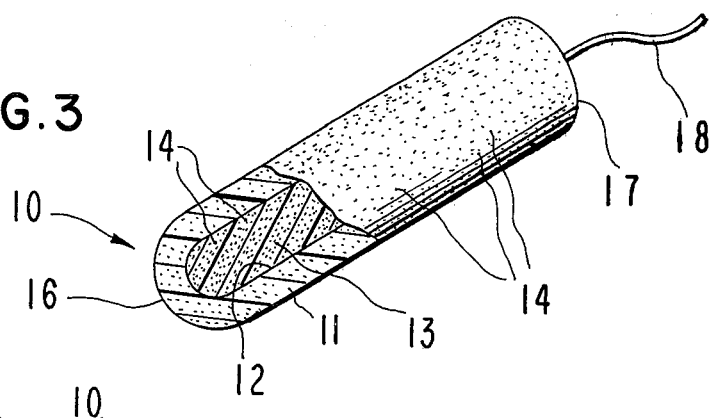
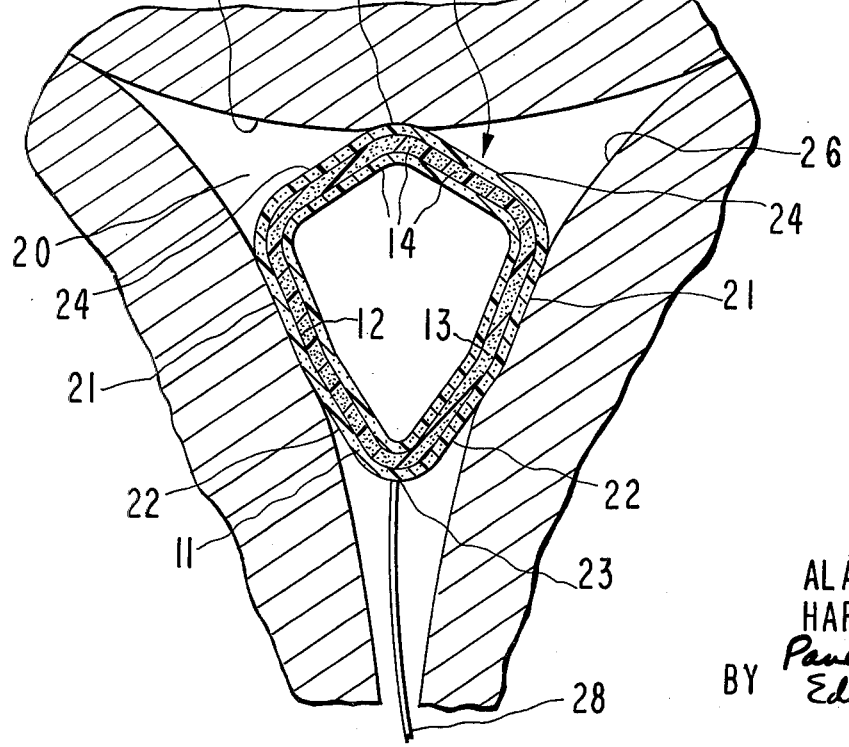
INVENTORS
ALAN S. MICHAELS
HAROLD M. LEEPER
BY Paul L. Sabatine &
Edward L. Mandell
ATTORNEY

NOVEL DRUG PERMEABLE WALL

CROSS REFERENCE TO RELATED APPLICATIONS

This application is a continuation-in-part of copending application Ser. No. 209,782, filed Dec. 20, 1971 and now abandoned.

BACKGROUND OF THE INVENTION

1. Field of the Invention

This invention relates to a novel drug-permeable polymeric wall adapted to release a drug at a controlled rate from a drug-containing reservoir to a body environment and to novel drug delivery devices including such a wall. It also relates to methods for increasing the permeability of polymers used to make such walls and methods for modifying the rate of drug release through such walls.

2. Description of Prior Art

Prior art drug delivery devices comprised of a drug dispersed in a solid matrix permeable to passage of the drug and surrounded by a polymer membrane, also permeable to passage of the drug but at a lower rate than through the matrix, have proven themselves capable of zero order drug release and represent a substantial improvement over previously proposed drug delivery devices. The drug release rate in these devices is controlled by using certain wall forming materials for releasing the drug, and the release rate for the drug is proportional to its diffusion coefficient in the wall and to the solubility of the drug in the wall. In making these drug delivery devices available to the art, these parameters are developed for each drug, and it has now been found that this can require a large number of wall forming materials for different drugs. This often adds considerable complexity to the design of drug delivery devices.

It is also known to the art to incorporate drug into certain types of liquid carriers, usually in microcapsule formulations, for example, as in U.S. Pat. No. 3,464,413. However, these microcapsules are not designed for the controlled release of drug for a prolonged period of time by using drug release rate controlling wall materials. The microcapsules are frequently crushable, and they merely function as drug carriers supplying their drug in bulk, and not in controlled amounts by rupture of the microcapsules. These types of capsules are not suitable for releasing drug at a controlled rate for a prolonged period of time.

The prior art also discloses incorporating conventional plasticizers in polymer walls of drug delivery devices (U.S. Pat. Nos. 3,630,200 and 3,538,214) to increase the flexibility of such walls.

SUMMARY OF THE INVENTION

A primary object of this invention is to provide means and methods for modifying the permeability of a drugpermeable polymeric wall adapted to release a drug at a controlled rate from a drug-containing reservoir to a body environment or a drug receptor site.

Another object of this invention is to provide drug permeable walls of unique polymeric composition which are adapted for use in drug delivery devices in which drug is released at a controlled rate from a drug-containing reservoir to a body environment by permeation through a polymeric wall. Correlatively yet another object is to provide improved drug delivery devices which include at least one of such walls.

The drug-permeable walls of this invention are adapted for use in the prior art devices which release a drug at a controlled, preferably substantially constant, rate from a reservoir comprising a carrier which is permeable to the drug and drug in an amount sufficient to maintain the concentration of drug in the carrier at saturation concentration during the life of the device to a body environment or drug receptor site by passing the drug through a drug release rate controlling polymer wall which is permeable to the drug but at a rate less than that of the carrier to the drug. They comprise a homogeneous mixture of (1) a polymer which is biologically compatible with said environment or site and maintains its integrity while in association therewith, has a glass transition temperature between about ambient (normal room) temperature and 150°C, a crystallinity in the range of about 5% and about 95% or is rubbery and is permeable to the drug at a rate less than the carrier of the device and (2) a polymeric additive selected from the group consisting of certain polyesters prepared from a glycol and a dibasic acid, polyethylene glycol, chlorinated polyethylene and copolymers of ethylene and vinyl esters or vinyl halides, the amount of said additive in the mixture being sufficient to make the permeability of the mixture to the drug substantially different than the permeability of the polymer to the drug but still less than the permeability of the carrier to the drug.

The methods of this invention involve mixing the above defined polymeric additive into the above defined polymers in various amounts which provide mixtures thereof having a predetermined range of permeabilities to the drug.

Other objects, features, and advantages of the invention will be apparent to those skilled in the art from the detailed description of the invention which follows, taken in conjunction with the drawings, and the accompanying claims.

BRIEF DESCRIPTION OF THE DRAWINGS

In the drawings, which are not drawn to scale, but rather are set forth to illustrate various embodiments of the invention:

FIG. 1 is a perspective, cross-sectional view of a drug delivery device of the invention depicting a wall surrounding a reservoir;

FIG. 2 is an enlarged fragmentary cross-sectional view of a drug delivery device of the invention illustrating two different walls surrounding a reservoir containing a drug;

FIG. 3 is a side, fragmentary view depicting a vaginal drug delivery device of the invention for releasing drug in a body orifice; and FIG. 4 is a frontal, fragmentary view of a uterine cavity showing a drug releasing intrauterine device positioned in the cavity;

In the drawings and specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Turning now to the drawings in detail, which are examples of various drug delivery devices of the invention, and which examples are not to be construed as limiting, one embodiment of a novel drug delivery device is indicated in FIGS. 1 and 2 by the number 10. In FIG. 1 drug delivery device 10 is comprised of a wall 11 surrounding a reservoir 12. Reservoir 12 is comprised of a drug carrier 13 as shown in FIG. 1 and it contains a drug 14, or a mixture of drugs. Drug carrier 13 is a solid and it is permeable to the passage of drug 14, as by diffusion and/or connection. Wall 11 is formed of a mixture of polymer, defined briefly supra and in detail infra permeable to the passage of drug 14, as by diffusion, and a permeability modifying additive also defined briefly supra and in detail infra that causes the permeability of the wall to be materially different than the permeability of said polymer by itself and likewise causes the rate of passage of drug 14 through wall 11 to be materially different than if wall 11 was formed only of said polymer. The rate of passage of drug 14 through wall 11 is lower than the rate of passage of drug 14 through solid drug carrier 13. Drug 14 consists of a portion which is dissolved in carrier 13 and an undissolved portion and is present within reservoir 12 in an amount sufficient to maintain a saturation concentration of drug in the carrier throughout the use period of the device.

In operation, solid drug carrier 13 serves as a reservoir 12 by supplying dissolved drug 14 to wall 11 as drug molecules move through the carrier to bathe the inner surface of wall 11. Drug 14 present at the drug carrier/wall interface dissolves in and migrates through the wall ultimately reaching the outer surface of wall 11. As drug 14 leaves drug carrier 13, undissolved drug present in reservoir 12 dissolves in solid carrier 13 to maintain a saturation concentration of drug in the carrier for continuously supplying drug at substantially the same rate to wall 11. Thus, a substantially zero order drug release rate of specifically defined magnitude is obtained.

In FIG. 2, wall 15 comprising the remainder of device 10 is formed of a material impermeable to the passage of drug 14. Reservoir 12 of FIG. 2 is comprised of a drug carrier 13 containing a drug 14 or a mixture of drugs. Carrier 13 of FIG. 2 is a liquid carrier and it is permeable to the passage of drug 14 as by diffusion, or by convection, or by an occurrence of both. As in the embodiment of FIG. 1 drug 14 is present in the reservoir as a dissolved portion and an undissolved portion in an amount sufficient to maintain saturation concentration in the carrier during the use period of the device.

In operation, carrier 13 serves as a reservoir by supplying dissolved drug 14 to wall 11 as molecules move through the carrier to bathe the inner surface of wall 11. Drug 14 present at the carrier/wall interface dissolves in and migrates through wall 11, the composition of which is the same as the composition of the wall of FIG. 1, ultimately reaching the outer surface of wall 11 for release to a drug receptor site. Wall 11 is substantially impermeable to carrier 13, and it remains in the reservoir. Additionally, the permeability of wall 11 per se to the diffusion of drug 14 is lower than the permeability of liquid drug carrier 13 to the diffusion of drug 14 and passage through wall 11 thus acts as the rate limiting step for drug release from device 10.

FIG. 3 illustrates another drug delivery device of the invention. In FIG. 3 there is illustrated a drug delivery device 10 designed for administering drug within a body opening, the vaginal canal, not shown. Drug delivery device 10 of FIG. 3 is comprised of a cylindrical body having a wall 11 surrounding a reservoir 12. The cylindrical body is provided with a rounded entrant end 16 and at the opposite end 17 with a pull string 18 for easy removal from the vaginal canal. Reservoir 12 is comprised of a drug carrier 13 containing drug 14. Drug carrier 13 is solid or liquid in nature. Drug carrier 13 is permeable, as by diffusion, to the passage of drug 14, which has limited solubility therein. As in the devices of FIGS. 1 and 2 drug 14 consists of a dissolved portion and an undissolved portion and is present in an amount sufficient to maintain saturation concentration in the carrier 13 for the useful life of the device. Wall 11 is made of a mixture of polymer and polymeric additive that is insoluble in body fluids, indigestible and non-erodible and it is permeable to the passage of drug 14, as by diffusion. In this device, as with the devices discussed above, wall 11 contains an effective amount of a permeability modifying additive that affects the rate of drug passage through wall 11, and the permeability of wall 11 to drug is lower than the permeability of carrier 13 to drug. Thus, passage of the drug through wall 11 is the rate controlling step for releasing drug from the drug delivery device.

In FIG. 4 there is graphically depicted an intrauterine contraceptive drug delivery device 10 prepared according to the spirit of the invention. Device 10, it will be seen, consists of a closed perimeter and an open central area and having geometric dimensions generally conforming to the internal shape of a uterus 20. The device generally has a pair of median sides 21 extending downwards into a second pair of sides 22 joined at an apex 23. The upper portion of device 10 has a pair of corresponding sides 24 joined at an apex 25. Device 10 is adapted to be located within the uterine cavity 20 and when positioned therein, it contacts the sides 26 as well as the fundus uteri 27. Device 10 is capable of being substantially straightened by passing through a hollow instrument for positioning it in uterus 20. The device is also equipped with a pair of nylon or surgical threads 28, attached to its trailing end for manually removing the device from the uterus.

Device 10 of FIG. 4 is comprised of a wall 11 housing a reservoir 12. Reservoir 12 is comprised of a drug carrier medium 13 containing a drug 14 in the portion's and amount hereinbefore described. The carrier confined in the reservoir serves several purposes for effectively releasing drug from the device. First, it contains a drug or a mixture of drug and it is permeable to the passage of drug so that drug in the carrier can migrate to wall 11. Secondly, the carrier contacts and bathes the inner surface of wall 11 for facilitating drug transfer from the carrier to the wall so that drug molecules can dissolve in and diffuse through the wall and migrate through it to the outer surface thereof. Thirdly, the carrier serves as a constant source of drug as it has a limited or varying degrees of solubility for drug or a mixture of drugs. Thus, the carrier is a constant source of drug because, as drug dissolves in the carrier and transfers from the carrier to the wall, undissolved drug dissolves in the carrier to insure a constant and uniform supply of drug until essentially all of the drug has been released by the device. This mechanism of continually replenishing the drug contributes to the device's ability to achieve a uniform substantially time independent release rate for the device throughout its use.

As in the above described embodiments wall 11 of the intrauterine contraceptive drug delivery device 10, is formed of a homogeneous mixture of release rate controlling polymer to continuously meter the flow of a contraceptively effective amount of a drug from reservoir 12 for release within uterus 20 and a release rate (permeability) additive whose presence in wall 11 materially affects the rate of drug release through the wall. That is, by controlling the amount of modifying agent in the wall the rate of drug release through the wall can be effectively controlled to predetermined rates, and this rate of drug release is lower than the passage of drug through and/or from the carrier, so that the former is the rate controlling step for drug release from the intrauterine contraceptive device. The depicted intrauterine drug delivery device is manufactured in a non-traumatising design for easy insertion into the uterine cavity. The device can be fabricated into assorted sizes, shapes, and thicknesses for adaptation to a wide variety of uteri.

While the above FIGS. 1 through 4 inclusive are illustrative of various drug delivery devices that can be made according to the invention, it is to be understood that these drug delivery devices are not to be construed as limiting, as the drug delivery devices of the invention can take a wide variety of shapes, sizes and forms for administering the drug at controlled rates to different areas of the body or to different drug receptor sites. For example, the invention includes external and internal drug delivery devices such as skin patches, sublingual or buccal drug delivery devices, peroral devices, arterial devices, nasal and ear drug delivery devices, suture materials, plastic heart valves, Starr-Edwards heart valves, hip joints, non-thrombogenic hydrocephalus shunt, bone pins, pessaries, prostheses, artificial glands, cervical rings, troches, intrauterine drug delivery devices of cylindrical, bullet, elliptical, circular, bulbous, loops, bows, or any other geometrical shape that readily lends itself to intrauterine placement such as Birnberg's Bow in U.S. Pat. No. 3,319,625; Comet in U.S. Pat. No. 3,256,878; Majzlin Spring in U.S. Pat. No. 3,397,691; Inhiband in U.S. Pat. No. 3,323,520; Bakunin in U.S. Pat. No. 3,405,711; Shamrock in U.S. Pat. No. 3,077,879; the ring with tail; Ota ring, and the like. In each instance, all of the drug delivery devices made according to the invention have a reservoir comprised of a drug and a drug carrier permeable to the passage of drug, as by diffusion and/or convection. The reservoir is surrounded by a wall, at least a portion of which is formed from a mixture of a polymer permeable to the passage of drug, as by diffusion, and a polymeric release rate modifying additive which significantly affects the rate of drug passage through the wall. The drug rate of release through the wall is lower than the rate of passage through the carrier, so that the drug release rate through the wall is the drug release rate controlling step. Also, all of the drug delivery devices are of appropriate known shapes and sizes for implantation, insertion or positioning in the desired body cavities or on tissues for administering of drug to the body or to a drug receptor site.

DETAILED DESCRIPTION OF THE INVENTION

In accordance with the practice of the present invention, it has now been found that the drug delivery devices which include the wall of the invention provide many important advantages over previously known drug delivery devices. One advantage of the device is the ease of construction of the drug delivery device by standard manufacturing techniques into devices of various sizes, shapes and forms for delivering drugs to a recipient. A more important advantage is that the invention wall may be used to provide a broad range of drug release rates by providing one or more devices having a reservoir, or more than one reservoir in a large multi-purpose device, wherein the reservoir contains a carrier or a mixture of carriers having varying degrees of solubility for a drug or a mixture of drugs and where the carrier simultaneously releases drug to the wall and dissolves replacement drug to maintain a constant supply of drug for release by the device.

Another important advantage of the invention resides in the drug delivery devices' ability to effectively control the rate of release of the drug from the device by providing a zero order ($dM_t/dt$ = constant) rate of drug release throughout the major portion of the drug release history. The drug time release pattern for the device of the invention is obtained by a selection of the drug release parameters, such as, the nature of the basic polymer component of the wall, the nature and amount of additive per area of wall, the nature of the drug carrier in the reservoir, and the kind of drug contained therein.

The above advantages and objects are achieved by the unique construction and operation of the device and its ability to transfer drug to a recipient or to a drug receptor site. In construction, the device can be viewed as a single unit constructed device comprising two structures acting in concert for effective drug administration to a host. One structure pertains to a wall formed of a drug release rate controlling polymer containing a drug release rate (permeability) modifying additive therein, and the other structure relates to a reservoir comprising a drug and a carrier of a material permeable to the passage of drug. The materials forming the wall and the drug carrier are chemically and structurally different within a single device and the rate of release of drug through the wall is lower than the rate of passage of drug in the drug carriers.

These two structures, comprising the unit drug delivery device, operate to effectively transfer drug from the device by first transferring drug from the carrier to the wall containing the release rate modifying additive, and secondly, by transferring drug through the wall to a drug recipient. The transfer of drug through the wall occurs by diffusion. In the diffusion process, the drug dissolves in the wall and then diffuses in the direction of lower chemical potential. At the second boundary, the outside of the wall, equilibrium is again established. When the boundary conditions on both sides of the wall are maintained constant, a steady state flux of the drug will be established which can be described by Fick's Law of Diffusion. The rate of passage of drug through the wall is generally dependent, in the case of diffusion, on the solubility of the drug in the wall, as well as on the diffusion coefficient. This means that selection of appropriate materials for fabricating the wall will be dependent on the particular wall, the media and the drug to be used.

The polymers which form the basic component of the wall are those which have physical and chemical properties suitable for the fabrication process and suitable for the use environment and through which the drug can pass at a controlled rate of release by the process of diffusion. In this regard they are biologically compatible with body fluids, tissues or organs, and essentially insoluble in body fluids, and non-erodible, with which they will come in contact. Generally, the use of rapidly dissolving materials or materials which are highly soluble, or which swell to lose or distort their predetermined shape, in body fluids is to be avoided since dissolution or loss of properties of the wall of the device would affect the constancy of the drug release, as well as the capability of the system to remain in place for certain uses for prolonged periods of time.

These polymers are approximately classified into three categories: (1) polymers whose glass transition temperatures are above room temperature (20°–150°C) and have low permeability to drugs because of low molecular mobility; (2) polymers which are partially crystalline (5–95%) and hence have low permeability to drugs; and (3) polymers which are rubbery, and whose glass transition temperatures are below room temperature, i.e. about 20°C. In the latter category these rubbery polymers may be thermoplastic or thermosetting in nature. Such polymers are commercially available and include polyvinyl chloride, polyvinylidene chloride, polyvinyl fluoride, polyvinylidene fluoride, polyvinyl acetate, polyvinyl butyral, polystyrene, cellulose acetate, cellulose nitrate, ethyl cellulose, cellulose acetate butyrate, cellulose acetate propionate, polyurethane, butadiene/acrylonitrile copolymer, chlorinated natural rubber, styrene/butadiene copolymer, ethylene/propylene copolymer, ethylene/vinyl acetate copolymer, ethylene/vinyl chloride copolymer, polyethylene, polypropylene and polyalkyl acrylates in which the alkyl group is of 2 to 4 carbon atoms.

The polymeric release rate modifying additives that are homogeneously mixed with the above described polymers to form the walls of this invention are essentially insoluble in body, that is, animal fluids, nonvolatile and nonleachable and nonextractable from the polymer once they are blended thereinto. These additives are commercially available and include: (1) essentially linear olefinically saturated polyesters having a number average molecular weight of less than about 20,000, preferably about 500 to about 8,000, of a diol of 2 to about 7 carbon atoms or polyethylene glycol and a dibasic carboxylic acid of about 6 to about 15 carbon atoms in which the terminating group is a carboxyacyl group of about 2 to about 18 carbon atoms or an alkoxy group of about 3 to about 15 carbon atoms. Such polyesters include those of the recurring general formula:

terminating groups are the acyl derivatives of fatty acids such as a lauryl, stearyl capryl and pelargonyl, acyl derivatives of aromatic acids such as benzoyl; and butoxy, octoxy, 2-ethylhexoxy, decoxy, nonoxy, isodecoxy and the like; (2) polyethylene glycols of about 200 to about 1,500 molecular weight; (3) ethylene-vinyl acetate copolymers of about 20 to about 40% by weight vinyl acetate and about 20,000 to about 30,000 number average molecular weight; (4) chlorinated polyethylene of about 25 to 45% by weight chlorine and about 20,000 to about 30,000 number average molecular weight; (5) ethylene-ethylacrylate copolymers of about 20% to about 40% by weight ethylacrylate and about 20,000 to about 30,000 number average molecular weight; and (6) ethylene-vinyl chloride copolymers of about 25% to about 45% by weight chlorine and about 20,000 to about 30,000 number average molecular weight.

The novel wall compositions of the invention are made by mixing one or more of the above described polymers with one or more of the above described additives. Such mixing may be carried out by conventional techniques and procedures well known in the art. The amount of additive in the mixture is sufficient to provide the mixture with a permeability to drug that is materially different, in nearly all instances materially greater, from the permeability of the polymer itself to drug. By varying the specific amount of additive mixtures of varying permeability may be readily made. Accordingly, permeability and drug release rate may be materially changed by a simple blending process rather than a complete change in the selection of polymer.

Generally the amount of polymeric drug release rate additive present in the mixture will be about 0.2 mg to 5.0 mg per cm², preferably 1 to 2 mg per cm², for a 1 to 5 mil thick wall, or about 0.016 g to 2.0 g per unit volume, that is, for each cc of wall. A typical additive concentration at these ranges, for example 0.1 g to 0.5 g for each cc of wall, will allow a corresponding drug release of 1 microgram to 100 micrograms per hour.

The term "reservoir" as used in the specification and the accompanying claims generally refers to a "drug", a "drug carrier" or to a "medium-containing drug", that constantly bathes the inner surface of the drug release rate controlling wall and supplies drug thereto. That is, the reservoir is comprised of a drug carrier

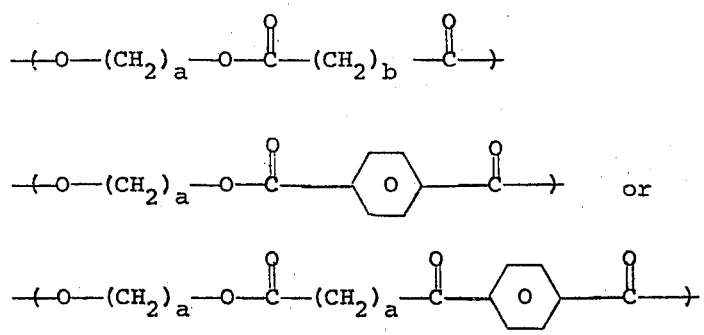

wherein $a$ is an integer from 2 to 4, inclusive, and $b$ is an integer from 4 to 13, inclusive. Typical diols which are used in such polyesters are alkylene glycols, e.g. ethylene glycol, diethylene glycol, triethylene glycol, propylene glycol, and alkane diols, e.g. 1, 3-butane diol, and 2, 2-dimethyl -1,3-propane diol. Representative of such dibasic carboxylic acids are adipic, azelaic, sebacic, phthalic, isophthalic, terephthalic, pimelic, α,ω-dodecanoic and α,ω-tridecanoic. Examples of such material saturated with dissolved drug, and undissolved drug in a form and amount sufficient to maintain a saturation concentration of drug throughout the carrier during the useful life of the device. The carrier is permeable to the passage of the drug as by diffusion and/or convection. The drug carrier medium used for the purpose of the invention is a solid, or a liquid, and it can be inorganic or organic, and of naturally occurring or synthetic origin. Examples of solid carriers comprised within the term solid are, for example, gelatin; starches; carbohydrates; solid extracts of Irish moss; ethylcellulose; cured polymers; silicone carbonate copolymers; hydrophilic polymers such as hydrophilic hydrogels of esters of acrylic acids; modified collagen; surface treated silicone rubbers; plasticized poly(vinylchloride); and the like. Representative of liquid carriers include ethylene glycol, liquid polyethylene glycols having a molecular weight of 200, 300, 400 and 600, fats and oils of plant, animal and marine origin such as almond oil, babassu oil, cocoa butter, corn oil, soybean oil, emulsions of gum arabic, water and ethyl cellulose, liquid glyceryl triesters of a lower molecular weight fatty acid, aqueous suspensions of poly(vinyl pyrrolidone), and the like. Further, for the purpose of this invention, the terms solid carrier and liquid carrier and the examples thereof are deemed as functional equivalents and they can also be generically termed "core" or "carrier". Remington's Pharmaceutical Sciences, pages 1627 to 1679, 1970, published by Mack Publishing Company, Easton, Pa.

The drug carrier medium comprising the reservoir, also has in addition to the properties described supra, limited solubility for contained drug or for a mixture of drugs. By limited solubility is meant that drug is soluble in given amounts in the carrier; that is, it comprises varying concentrations of drug dissolved in the carrier. Essentially, there is also an excess amount of undissolved drug present in the carrier. These varying limited solubility concentrations include solubilities such as soluble, sparingly soluble, slightly soluble, very slightly soluble, and almost practically insoluble. Generally, on a weight basis at 25°C, the amount of drug dissolved in a carrier comprises a range of solubility of drug in the carrier of 1 part of drug to about 10 parts to 15,000 parts of carrier. Presently, when desired to obtain a zero order rate of drug release, the drug incorporated in the carrier is preferably sparingly soluble so as to maintain substantially the same thermodynamic activity of the drug throughout the release period.

The composition wall 11 is chemically and/or structurally different than the composition of the carrier. Both the wall and the carrier are permeable to the passage of drug but the rate of flow through wall 11 is lower than the rate through the carrier. Thus, the rate of passage of drug through the wall is the rate release controlling step for the device. Generally, for the practice of this invention, the ratio of the drug release rate through the drug carrier of the reservoir to the drug release rate through the wall containing the modifier should be from 1000:1 to 2:1 and preferably from 10:1 to 200:1. Of course, the invention is not limited to these release rates, or compositional ranges, as the invention comprises lower or higher release rates from the drug carrier and lower and higher rates through the wall with the release rate through the wall lower than the release rate of the drug carrier. Thus, the invention provides that devices comprised of a carrier with various amounts of additive in the wall and activated by diffusion, can give different dosages of a drug by varying the characteristics of the respective materials to give controlled administration of a drug.

For the above discussed devices, because the reservoir serves to transfer drug molecules to all areas of the wall, the wall of the drug delivery system housing the reservoir remains substantially at the thermodynamic activity corresponding to that of the drug until substantially all of the drug has been released from the reservoir. Ordinarily, one would expect drug migration from the reservoir to cease when sufficient drug has entered the wall to establish an equilibrium; however, when the drug delivery system is in contact with body tissues or fluids, drug molecules are continuously removed from the outer surface of the wall. For optimum results, the rate of release of the drug through the wall should be less than the rate of clearance of migrated drug from the external surface of the device. This ensures that the drug administration rate is dependent on the rate of release of drug through the wall which can be controlled, rather than upon clearance of drug from the device in vivo, which can vary.

The rate of release of a drug through various materials, for example the release rate controlling wall, or a carrier, can easily be determined by those skilled in the art by standard procedures. In this manner, particular materials used as the device's wall for use as the drug release rate controlling barrier for release of drug from the reservoirs, as the carrier, can be scientifically selected. Various techniques, such as the transmission method, the sorption-desorption method, and the like, can be used as measurers of permeability. One technique that has been found to be accepted is to cast or hot press a film of the wall forming material to a thickness in the range of 1 to 60 mils. The film is used as a barrier between a rapidly stirred, for example, about 150 r.p.m., saturated solution of the drug and a rapidly stirred solvent bath, both maintained at constant temperature, typically 37°C. Samples are periodically withdrawn from the solvent bath and analyzed for drug concentration. By plotting the agent's concentration in the solvent bath versus time, the permeability constant P of the material is determined by Fick's First Law of Diffusion.

$$\text{Slope of plot} = \frac{Q_1 - Q_2}{t_1 - t_2} = P \frac{AC}{h}$$

wherein
$Q_1$ = cumulative amount of drug in solvent in micrograms at $t_1$
$Q_2$ = cumulative amount of drug in solvent in micrograms at $t_2$
$t_1$ = elapsed time to first sample i.e. $Q_1$
$t_2$ = elapsed time to second sample i.e. $Q_2$
$A$ = area of membrane in cm$^2$
$C$ = initial concentration of drug
$h$ = thickness of membrane in cm.
By determining the slope of the plot, $$\text{i.e.} \frac{Q_1 - Q_2}{t_1 - t_2}$$

and solving the equation using the known or measured values of $A$, $C$, and $h$, the permeability P constant in cm$^2$/time of the material for a given drug is readily determined. Procedures for determining the rate of drug release through the carrier can be easily used by following standard techniques known to the art as recorded in J. Pharm. Sci., Vol. 52, pages 1145 to 1149, 1963; ibid. Vol. 53, pages 793 to 802, 1964; ibid. Vol. 54, pages 1459 to 1464, 1965; ibid. Vol. 55, pages 840 to 843 and 1224 to 1239, 1966; Encyl. Polymer Sci. Technol., Vol. 5 and 9, pages 65 to 82 and 794 to 807, 1968; the references cited therein, and the like.

The solubility of a drug in a liquid carrier can be determined by various art known techniques. One method consists in preparing a composition of the given drug and ascertaining by analysis the amount of drug present in a definite quantity of the liquid carrier. A simple apparatus for this purpose consists of a test tube of medium size fastened upright in a water bath maintained at constant temperature. The liquid carrier and drug are placed in the tube and stirred by means of a motor driven rotating glass spiral. After a given period of stirring, a definite weight of the liquid carrier is analyzed and the stirring continued for an additional period of time. If the analysis shows no increase of dissolved substance after the second period of stirring, the results are taken as the degree of solubility of the drug in the liquid carrier. Numerous other methods are available for the determination of the degree of solubility of a drug in a liquid carrier. Typical methods used for the measurement of solubility are chemical analysis, measurement of density, refractive index, electrical conductivity, and the like. Details of various methods for determining solubilities are described in United States Public Health Service Bulletin No. 67 of the Hygienic Laboratory; Encyclopedia of Science and Technology, Vol. 12, pages 542 to 556, 1971, McGraw-Hill, Inc., Encyclopaedic Dictionary of Physics, Vol. 6, pages 545 to 557, 1962, Pergamon Press, Inc., and the like.

The solubility of the drug in a solid carrier used for making a device broadly is determined by preparing a saturated solution of a given drug and ascertaining, by analysis, the amount present in a definite area of the carrier. For example, the solubility of the drug in the carrier is determined by first equilibrating the carrier material with a saturated solution of the drug at a known, temperature, for example 37°C, or with a pure liquid drug if the drug is a liquid at 37°C. Next, drug is desorbed from the saturated carrier material with a suitable solvent for the drug. The resultant solution for the drug then is analyzed by standard techniques such as ultraviolet, visible spectrophotometry, refractive index, polarography, electrical conductivity and the like, and calculating from the data the concentration, or solubility of the drug in the solid carrier.

The diffusion coefficient of a drug in a polymer is determined by techniques known to the art such as the transient state sorption-desorption method. The method is carried out by first soaking the membrane in a concentrated solution of a drug for sufficient time to reach equilibrium. Next, the membrane is removed from the solution and its surface wiped or rinsed to remove adhering drug solution. The membrane is then placed into a flask containing drug-free water and the amount of drug subsequently present in the water is measured at regular intervals as it comes out of the membrane until no more drug leaves the membrane. This procedure and the method for calculating the diffusion coefficient using this procedure is described in Diffusion in Polymers, Edited by Crank, J. and Park, G. S., Chapter 1, pages 1 to 37, 1960, published by Academic Press, Inc., London; and in Diffusion In Solids, Liquids, Gasses, by Jost, W., Chapter 1, pages 35 to 39, 1960, published by Academic Press, Inc., New York; and the references cited therein. The diffusion coefficient of a drug in a membrane can also be experimentally determined by using similar procedures as described in Proc. Roy. Sci. London, Ser. A, Vol. 148, page 1935; and J. Pharm. Sci., Vol. 55, pages 1224 to 1229, 1966.

The solubility of a drug in the wall of a device broadly is determined by preparing a saturated solution of a given drug and ascertaining, by analysis, the amount present in a definite area of the wall. For example, the solubility of the drug in the wall is determined by first equilibrating the wall material with a measured saturated solution of the agent at a known temperature and pressure, for example 37°C and one atmosphere. Next, agent is desorbed from the saturated wall material with a suitable solvent for the agent. The resultant solution for the agent then is analyzed by standard techniques such as ultraviolet, visible spectrophotometry, refractive index, polarography, electrical conductivity and the like, and calculating from the data the concentration, or solubility of the agent in the material.

Using the procedures and formulas above described, one skilled in the art can design a drug dispensing device according to the invention by ascertaining the properties of the wall and carrier and then fabricating the device by selecting a carrier in which the drug has ascertained solubility and which is permeable to the drug but at a higher rate than the permeability of the wall to the drug. For example, by using the permeability coefficient, which is determined by using the above procedures and formulas, and which permeability coefficient is defined as the product of the diffusion coefficient, $D_w$, of the drug in the wall and a distribution coefficient, K, which is a ratio of the solubility of the drug in the wall to the solubility of the drug in the saturated solution, the selection of materials for forming the wall and the carrier can be made for making a device according to the invention. For purposes of comparing the permeability of the wall to that of the liquid carrier, it is convenient to define the permeability as follows: $P_w = PC = D_w S_w$ wherein P, C and $D_w$ have the meaning as above described and $S_w$ is the solubility of the drug in the wall. The permeability of the carrier to the drug can similarly be defined as $P_c = D_c S_c$ wherein $D_c$ and $S_c$ are the diffusion coefficient and the solubility of the drug in the carrier. The solubility, $S_c$, can be determined by cited methods. The diffusion coefficients of the drug in carriers will be in the range of $10^{-6}$ to $10^{-5}$ cm$^2$/sec. The diffusion coefficient of the drug in the wall will be in the range of $10^{-10}$ to $10^{-8}$ cm$^2$/sec. Thus, a selection of carrier materials such that $P_c > P_w$, preferably $P_c \geq 5 P_w$, is ascertained for preparing a delivery device. The symbols used herein have the conventional meaning, for example, the symbol ">" means greater than and the symbol "$\geq$" means greater than or equal to.

In the specification and the accompanying claims, the term "drug", broadly includes physiologically or pharmacologically active substances for producing a localized or systemic effect or effects in mammals including humans and primates, avians such as chicken and turkeys; valuable domestic household, sport or farm animals such as horses, dogs, cats, cattle, sheep and the like; or for administering to laboratory animals such as mice, monkeys, rats, guinea pigs; and the like. That is, the novel drug delivery device can be used for administering drugs that are physiologically or pharmacologically active at a point in near relation to the drug delivery device, or, for administering a systemically active drug which will produce a physiological or pharmacological response at a site remote from the point of application of the drug delivery device. The active drugs that can be administered by the drug delivery device of the invention include, without limitation: for example, drugs acting on the central nervous system, such as sedatives, hypnotics, psychic energizers, tranquilizers, and the like, drugs such as analgesics, antipyretics, antispasmodics, antimicrobials, hormonal agents, steroids, cardiovascular drugs, diuretics, neoplastic agents, hypoglycemic agents, and the like. Typical drugs are described in The Pharmacological Basis of Therapeutics, by Goodman and Gilman, 1970, Macmillan. Also, the drugs can be present as the pharmacologically acceptable derivatives, such as ethers, esters, amides, acetals, etc. that lend themselves to passage into the circulatory system. For highly water soluble drugs, it is preferable that the wall or the reservoir, or both be formed from a material that is substantially impermeable to water to essentially prevent dilution of the drug by absorption of body fluids into the device with an accompanying decrease in drug release rate. These derivatives can be prepared by art known techniques and then used in the practice of the invention. Of course, the drug derivative should be such as to convert to the active drug within the body through the action of body enzymes assisted transformations, pH, specific organ activities, and the like.

The amount of drug present in the reservoir, whether dissolved, partially dissolved or undissolved, is generally non-limited and it is an amount equal to or larger than the amount of a drug that on its release from the device is effective for bringing about the drug's physiological or pharmacological local or systemic effects. For example, the amount of drug present in the reservoir of a drug delivery device when the device is used for a period of time to achieve local or systemic effect is for various drugs, such as 11-desmethoxyreserpine about 5 to 140 mg in the reservoir; for aceptophenazine an amount in the reservoir of 100 to 400 mg; for methoxypromazine about 600 to 750 mg in the reservoir; for emcylamate a reservoir amount of 1.5 to 2.0 gm; for phenylglycodol a reservoir amount of 1.5 to 1.9 gm; about 160 to 250 mg of butabarbital in the reservoir; about 150 to 170 mg of chloradiazepoxide; from 0.5 to 1.2 gm of methsuximide; from 0.7 to 1.9 gm of ethosuximide; from 20 to 40 mg of hydrolazine; about 50 to 100 mg of totazoline; and the like. Generally, the drug delivery devices made according to the invention can contain from about 250 nanograms to 50 grams of drug for releasing it at a controlled rate of from about 25 nanograms to about 25 grams of drug or larger amounts per day. Of course, other devices containing different amounts of drug for use for different time periods such as a week, month and year are also readily made by the invention.

It will be appreciated by those versed in the art that the unique drug delivery device of this invention can provide for the programmed delivery of drug at a rate of delivery characterized by a zero order time dependence for prolonged period of time; and, that the device therefore lends itself to administering an effective amount of drug needed for a therapeutic effect while essentially avoiding the presence of excessive amount of drug at the needed biological site. By a prolonged period of time is meant, as used herein, periods that embrace the time needed for a fast acting drug to effect its end up to periods that embrace the continual, uninterrupted, repetitious time of a long term drug delivery device. For example, the prolonged time can be one hour or more for drugs, like local anesthetics, analgesics, prostaglandins or the like, that are effective in nanogram and milligram amounts, or the like, to 3 years or longer for steroids released within the uterine cavity. Other examples include wherein the amount of drug in the reservoir can be 100 to 300 mg of thiopropazate for releasing 15 to 30 mg over a 24 hour period; 200 to 400 mg in the reservoir of phenyltoloxamine for a release of 150 to 200 mg of papaverine in the reservoir for a topical release 30 to 75 mg over a 24 hour period; 2.5 g to 4.0 g of mephenoxalone for a release of 1.0 to 1.5 g per day; 15 to 25 mg of tranylcypromane for a release of 10 to 15 mg as the standard dose; 1 to 2 gm of trimethadione present in the reservoir for a release administration of 0.5 to 1.0 g per day; prostaglandins for example $PGE_1$, $PGE_2$, $PGA_1$, $PGF_{2\alpha}$ in amounts of 0.5 mg to 10 mg for release of 1 ng to 100 ng and the like; for progestogen or progesterone the administration in the uterus of 10 to 200 $\mu$g per day for release for 1 year to 3 years as an antifertility agent in a mature, child-bearing woman; an oral device administering 300 mg to 600 mg per day of analgesic acetaminophen to a 60 to 70 kg adult male; and the like.

The drug delivery devices of the invention are easily fabricated by using standard techniques. For example, in one embodiment, the reservoir comprising the carrier and the drug is fabricated by standard techniques. For example, in one embodiment a precured liquid polymer can be mixed with the drug in solid, semi-solid, or liquid forms at the time of mixing, and then distributed therethrough by conventional methods, such as ballmilling, calendering, stirring, shaking, rollmilling, and the like, followed by curing to yield a solid carrier. Next, the solid carrier is coated by spraying, dipping, and the like with a material that contains a known concentration of drug release rate additive and can form the wall of the device. In another embodiment a pre-polymer and the drug are mixed and then charged into a drug release rate controlling wall that also contains known amounts of a drug release rate additive or a mixture of additives and then cured into a solid, and sealed therein. In another embodiment solid drug particles and solid carrier particles are compressed into a carrier and then charged into a wall to form a novel drug delivery device.

In another embodiment a liquid, pre-cured material and the drug are mixed charged into and cured in a highly permeable tube that is positioned within a release rate controlling wall. Alternatively, the tube can be coated with the wall material, or a prepolymer can be cast around the tube and finally cured to form the wall. The device can also be manufactured by first forming a mixture comprised of an additive, a resin and a solvent, casting the mixture as a film, and then evaporating the solvent and drying the film to produce a drug release rate membrane that can be laminated with drug confined between the laminae.

The wall material forming the device and having the reservoir contained therein can be formed to a given drug design by molding, casting, pressing, extruding, drawing, rotational molding, compression and transfer molding, or like standard processes of manufacture. Also, depending on the material used to form the wall, a monomers may be cured at this stage of manufacture. The ability to design and shape the wall into tubes, rods, discs, films, rings and other highly reproducible shapes of controllable composition, readily results in fabrication of drug delivery devices with controlled characteristics and thus overcomes a significant disadvantage of previously described devices. Other standard procedures, as described in Modern Plastics Encyclopedia, Vol. 46, pages 62 to 70, 1969; Plastic Technology, by Swanson, R. S., pages 59 to 229, 1965, published by McKnight and McKnight Publishing Col, Bloomington, Ill.; well known to those skilled in the art can be used to fabricate the drug delivery device of the invention.

The following examples are merely illustrative of the present invention and they should not be considered as limiting the scope of the invention in any way, as these examples and other equivalents thereof will become apparent to those versed in the art in the light of the present disclosure, drawings and the accompanying claims.

EXAMPLE 1

A drug delivery implant device shaped like a rectangle and comprised of a reservoir containing a drug in a carrier surrounded by a drug release rate wall containing a drug release rate modifying additive is manufactured as follows: first, 100 parts by weight of suspension grade poly(vinylchloride) resin is mixed with 60 parts by weight of a polyester modifier of butylene glycol and adipic acid terminated with stearic acid of 2000 m.w. and the two mixed ingredients dissolved in 700 parts by weight of tetrahydrofuran to form a solution with a viscosity of about 5000 centipoises. Next, a film is formed by a doctor blade coating the solution onto a glass plate and allowing the solvent to air evaporate. The film is completely dried in an air oven at 50°C for several hours. A drug delivery device is formed by charging steroid dispersed in an aqueous methyl cellulose carrier between two layers of the film and heat sealing the contacting edges to form a drug implant device.

EXAMPLE 2

A drug delivery device for administering drug comprised of a wall surrounding a reservoir containing a drug is formed as follows: first, 100 parts of plastisol grade poly(vinyl chloride) is mixed with 100 parts of a liquid polyester modifier and 2 parts of di-octyl tin maleate and the ingredients mixed on a three-roll mill. The polyester modifier is a condensation polymer of 850 m.w. and is made from triethylene glycol and azelaic acid terminated with 2-ethylhexanol. The result is a thick cream which is cast by standard means, knife coating, on a siliconized paper substrate. The cast film is hot set by heating at 350°F for five minutes to produce a transparent, glass clear film. The film is then cut into predetermined shape and used to surround a reservoir comprised of pilocarpine in an alginic acid gel carrier.

EXAMPLE 3

A drug delivery device comprised of a drug release rate wall surrounding and housing a reservoir containing a drug is manufactured as follows: to 100 phr (parts per hundred) of polyvinyl acetate is added 25 phr of a liquid polyester modifier (a condensation polymer of propylene glycol and terephthalic acid terminated by dodecyl alcohol, the polyester having a m.w. of 8,000) and 600 parts of methyl ethyl ketone and the ingredients are mixed until a clear homogeneous solution is attained. The resulting solution is then spread on a glass plate with a coating knife and the ketone is allowed to evaporate at room temperature. Final traces of solvent ketone are removed by heating to 40°C for 4 hours in a vacuum oven. The resulting flexible film is stripped from the plate and used as a barrier membrane in the construction of drug delivery systems.

EXAMPLE 4

Following the procedure set forth in Example 1 a drug delivery device is prepared by repeating the described procedure except that 100 parts of polyvinylidene chloride and 35 parts of a polyester modifier, comprised of a condensation polymer of polyethylene glycol and phthalic anhydride terminated by stearic acid and m.w. 2,500 are dissolved in tetrahydrofuran, the membrane being made as described in Example 1.

EXAMPLE 5

Four hundred grams of low density (1.18) polyethylene is added to a laboratory size rubber and plastics mill (rolls 6 inches diameter, 13 inches wide) and milled for 3 minutes at 165°C. At this point is added 60 grams of a copolymer of ethylene and vinyl acetate of number average molecular weight 28,500 and a weight ratio of ethylene/vinyl acetate in the copolymer of 74/26. Milling is continued for 15 minutes to blend the modifier into the polyethylene. The resulting modified polyethylene is then extruded through a blow-film die to film thickness of 2.5 mils. This film is then used as a barrier membrane in a drug delivery system.

EXAMPLE 6

Ten grams of cellulose acetate of 38.6% acetyl content and 1.5 grams of polyethylene glycol of m.w. 800 are dissolved in dimethyl formamide and the resulting modified cellulose acetate is cast as a film from this solution onto a teflon belt and is stripped off, when dry, as a 2 mil thick film, which is then used as a barrier membrane for controlled drug delivery.

EXAMPLE 7

Five hundred grams of isotactic polypropylene are milled for 3 minutes at 175°C on a standard 6 inches × 13 inches laboratory mill and to this mass of polypropylene is added 48 grams of chlorinated polyethylene of molecular weight 22,000 and chlorine content of 34.6%. Milling is continued for 15 minutes at 175°C to effect homogenization. The modified polypropylene is then removed from the mill and is extruded through a flat die into a film 4 mils in thickness. This film is then used as a barrier membrane for controlled delivery of drug.

EXAMPLE 8

Six hundred grams of a copolymer of butadiene and acrylonitrile of 32% acrylonitrile content is mixed for 6 minutes at 65°C on a standard 6 inches × 13 inches laboratory rubber mill. At this point, at which time the rubber is smoothly banded on the mill rolls, 120 grams of a liquid polyester is added over a period of 6 minutes. The rubbery copolymer is cut and folded over intermittently to assure good blending of the polyester, which is made from a condensation reaction of 1,3-butanediol with sebacic acid and terminated with n-octanol to give a molecular weight of 3,400. The resulting modified rubbery polymer is compression molded at 120°C into a 4 mil film. This film is then used as a membrane barrier for controlled release of drug.

EXAMPLE 9

Four hundred grams of a copolymer of 95% ethylene and 5% propylene, by weight, is added to a standard 6 inches × 13 inches rubber roll mill and is milled for 3 minutes at 160°C. To the copolymer is then added 40 grams of a copolymer of ethylene and ethyl acrylate of 18% ethyl acrylate content and number average molecular weight 30,000. Milling is continued for 15 minutes and the resulting modified copolymer is removed from the mill and pressed between heated (160°C) platens into a film 4 mils thick. The platens are cooled while the film is under pressure, the pressure is released, and the film is stripped off. The film is then ready for use as a barrier membrane for controlled delivery of drugs.

EXAMPLE 10

Five hundred grams of low density (1.18) polyethylene is added to a laboratory size rubber and plastics mill (rolls 6 inches × 13 inches) and milled for 3 minutes at 165°C. At this point is added 60 grams of a copolymer of ethylene and vinyl chloride of number average molecular weight 26,000 and a chlorine content of 36%. Milling is continued for 15 minutes to blend the modifier into the polyethylene. The resulting modified polyethylene is then extruded through a blow-film die to a film thickness of 2.0 mils. This film is then used as a barrier membrane in a drug delivery system.

In Table 1 there is set forth the drug release rate results obtained by varying the amount of additive present in a wall of a delivery device.

Table 1

| Wall | Modifier | Amount | Drug Release Rate Micrograms per hr. |
|---|---|---|---|
| PVC① | Polyester | 100 | 9 |
| ″ | ″ | 50 | 1 |
| PVC② | Condensation polymer of adipic acid, a glycol, terminated by a monocarboxylic acid | 100 | 19 |
| ″ | ″ | 75 | 8 |
| PVC① | ″ | 100 | 16 |
| ″ | ″ | 75 | 6 |
| ″ | ″ | 50 | 2 |

In Table 1, PVC① is commercially available poly(vinyl chloride) sold as PVC-450 by Diamond-Shamrock Co., PVC② is poly(vinyl chloride) Geon 103-EP as sold by the B. F. Goodrich Chemical Company.

It will be understood to those versed in the art in the light of the present specification, drawings and accompanying claims that the invention makes available to the art both a novel and useful drug delivery device for administering a drug to produce a local or systemic physiologic or pharmacologic effect; as, the rate of release of drug administered from the device can be controlled to produce these effects, while simultaneously lessening or overcoming the undesirable effects frequently associated with the administration of drugs by prior art methods. It will be further understood to those versed in the art that many different embodiments of this invention can be made without departing from the spirit and the scope of the invention. Accordingly, it is to be understood that the invention is not to be construed as limited, but it embraces all equivalents inherent therein.

We claim:

1. In a drug delivery device for continuously administering a drug at a controlled rate for a prolonged period of time to a body site, said device comprising a reservoir containing said drug and a carrier permeable to said drug, the amount of said drug being sufficient to maintain saturation within said carrier during said prolonged period, and a wall surrounding said reservoir which is permeable to the drug but at a rate less than that of the carrier, whereby the drug is released from the reservoir by diffusion through the wall in which the drug dissolves in the material forming the wall and moves therethrough in the direction of lower chemical potential, the improvement comprising forming the wall from a composition comprising a mixture of:
   A. a polymer which is rubbery with a glass transition temperature below about 20°C, or is glassy having a glass transition temperature between about 20°C and about 150°C, or has a crystallinity between about 5% and about 95%; and
   B. a polymeric additive which is essentially insoluble in body fluids, is nonvolatile and nonleachable and nonextractable from the polymer under the use conditions of the composition and is selected from the group consisting of:
      a. essentially linear olefinically saturated polyesters having a number average molecular weight of about 500 to about 8,000 of a diol of 2 to about 7 carbon atoms or polyethylene glycol and a dibasic carboxylic acid of about 6 to about 15 carbon atoms in which the terminating group is a carboxyacyl group of about 2 to about 18 carbon atoms or an alkoxy group of about 3 to about 15 carbon atoms;
      b. polyethylene glycols of about 200 to about 1,500 molecular weight;
      c. ethylene-vinyl acetate copolymers of about 20% to about 40% by weight vinyl acetate and about 20,000 to about 30,000 number average molecular weight;
      d. chlorinated polyethylene of about 25% to 45% by weight chlorine and about 20,000 to about 30,000 number average molecular weight;
      e. ethylene-ethylacrylate copolymers of about 20% to about 40% by weight ethylacrylate and about 20,000 to about 30,000 number average molecular weight; and
      f. ethylene-vinyl chloride copolymers of about 25% to about 45% by weight chlorine and about 20,000 to about 30,000 number average molecular weight, the amount of additive in the mixture being sufficient to make the permeability of the composition of the drug substantially different than the permeability of the polymer to drug but less than the permeability of the carrier to drug, said composition being biologically compatible with the site, essentially non-erodible, essentially insoluble in body fluids, and, if the drug is highly water soluble, substantially impermeable to water to essentially prevent dilution of the drug by absorption of body fluids into the reservoir.

2. The improvement of claim 1 wherein said polymer is selected from the group consisting of polyvinyl chloride, polyvinylidene chloride, polyvinyl fluoride, polyvinylidene fluoride, polyvinyl acetate, polyvinyl butyral, polystyrene, cellulose acetate, cellulose nitrate, ethyl cellulose, cellulose acetate butyrate, cellulose acetate propionate, polyurethane, butadiene/acrylonitrile copolymer, chlorinated natural rubber, styrene/- butadiene copolymer, ethylene/propylene copolymer, ethylene/vinyl acetate copolymer, ethylene/vinyl chloride copolymer, polyethylene, polypropylene and polyalkyl acrylates in which the alkyl group is of 2 to 4 carbon atoms.

3. The improvement of claim 1 wherein said amount of additive is 1 to 2 mg per cm² of wall.

4. The improvement of claim 2 wherein the amount of additive is 1 to 2 mg per cm² of wall.

5. The improvement of claim 1 wherein said polyester is of the recurring formula:

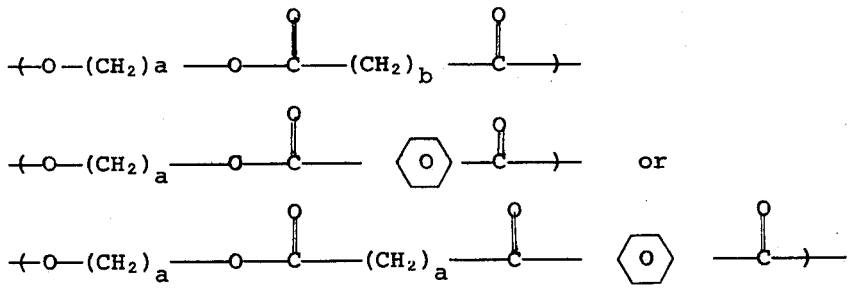

wherein $a$ is an integer from 2 to 4, inclusive, and $b$ is an integer from 4 to 13, inclusive.

6. The improvement of claim 1 wherein said amount of additive is about 0.2 mg to 5 mg per cm² of wall.

7. The improvement of claim 1 wherein the polymer is ethylene/vinyl acetate copolymer and the polymeric additive is an essentially linear olefinically saturated polyester having a recurring general formula

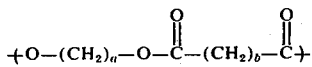

or wherein $a$ is an integer from 2 to 4, inclusive, and $b$ is an integer from 4 to 13, inclusive.

* * * * *